United States Patent [19]

Stone

[11] Patent Number: 4,666,429
[45] Date of Patent: May 19, 1987

[54] INFUSION DEVICE HAVING IMPROVED VALVING APPARATUS

[75] Inventor: Frederick L. Stone, Boulder, Colo.

[73] Assignee: Intelligent Medicine, Inc., Denver, Colo.

[21] Appl. No.: 833,003

[22] Filed: Feb. 26, 1986

[51] Int. Cl.$^4$ .................. A61M 37/00; A61M 5/005
[52] U.S. Cl. ...................................... 604/83; 604/247
[58] Field of Search ............... 604/83, 247, 32, 248, 604/249, 34, 246; 128/766

[56] References Cited

U.S. PATENT DOCUMENTS

| | | | |
|---|---|---|---|
| 1,973,845 | 9/1934 | Chenoweth | 604/32 |
| 3,416,567 | 12/1968 | Von Dardel et al. | 604/34 |
| 3,572,375 | 3/1971 | Rosenberg | 604/247 |
| 3,859,985 | 1/1975 | Eckhart | 604/248 |
| 4,063,555 | 12/1977 | Ulinder | 604/247 |
| 4,106,491 | 8/1978 | Guerra | 128/766 |
| 4,143,853 | 3/1979 | Abramson | 604/246 |
| 4,210,178 | 7/1980 | Morse et al. | 604/249 |
| 4,346,704 | 8/1982 | Kulle | 604/247 |
| 4,439,182 | 3/1984 | Huang | 604/247 |
| 4,447,230 | 5/1984 | Gula et al. | 604/247 |

*Primary Examiner*—C. Fred Rosenbaum
*Assistant Examiner*—Gene B. Kartchner
*Attorney, Agent, or Firm*—Robert E. Harris

[57] ABSTRACT

An infusion device is disclosed having an improved valving apparatus with the valving apparatus being configured to substantially preclude formation of volumetric dead spaces. The valving apparatus is typically utilized to allow introduction of one or more secondary fluids, such as drugs, into a patient during normal infusion of the primary fluid into the patient, with such insertion being effected through a secondary conduit connected to the primary infusion conduit through the valving apparatus. The valving apparatus includes a movable element that is positioned adjacent to the inner wall of the primary conduit so that the movable element forms a one-way valve thereat. The movable element is partially displaced due to flow of secondary fluid through the secondary conduit toward the primary conduit to thereby allow the secondary fluid to pass by the movable element and enter the primary conduit, but the movable element cannot be displaced by flow within the primary conduit and therefore prevents passage of fluids through the valving apparatus from the primary conduit to the secondary conduit. When not displaced due to flow of secondary fluid through the valving apparatus into the primary conduit, the movable element is positioned near the inner wall of the primary conduit to substantially preclude formation of volumetric dead spaces thereat.

11 Claims, 23 Drawing Figures

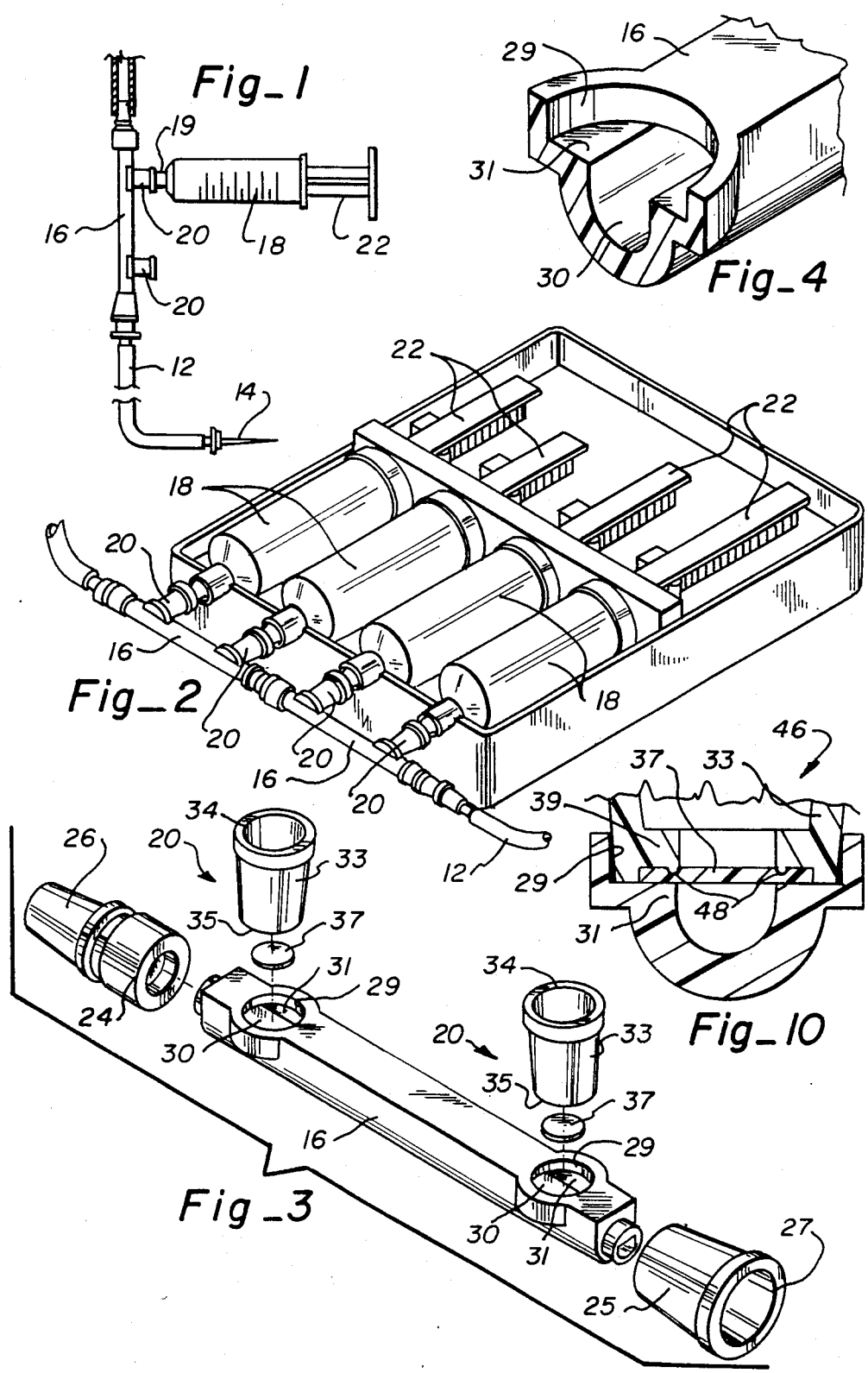

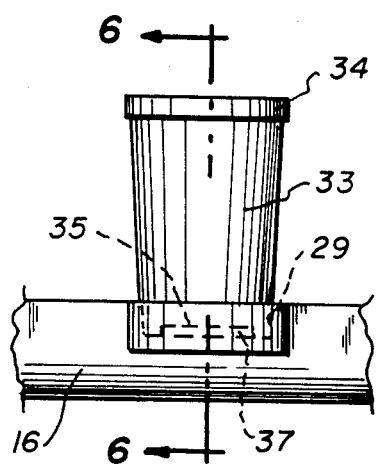
Fig_5
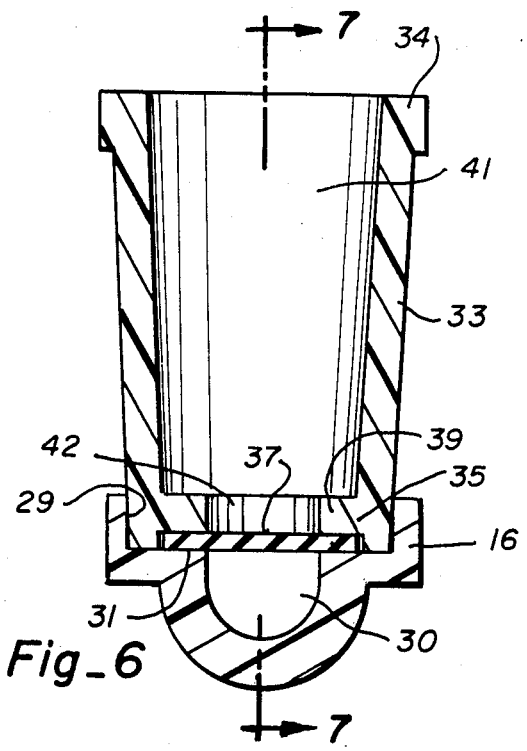
Fig_6
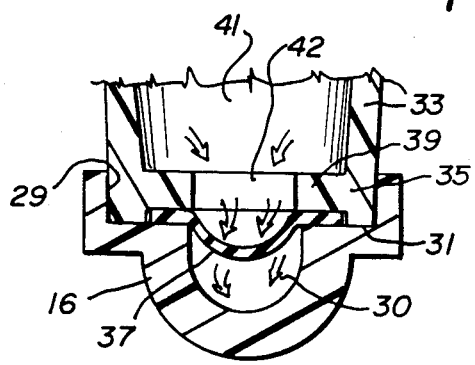
Fig_8
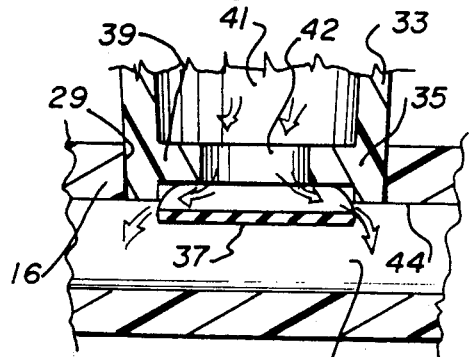
Fig_9
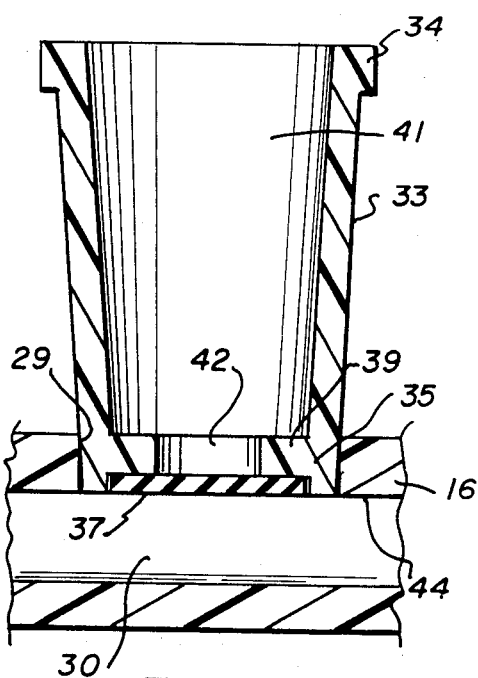
Fig_7

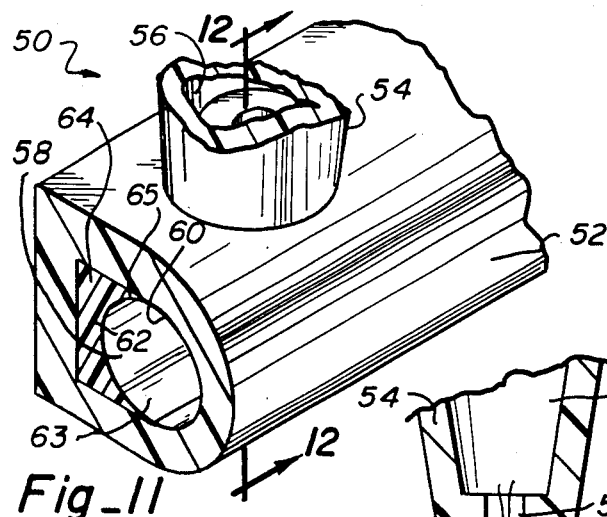
Fig_11
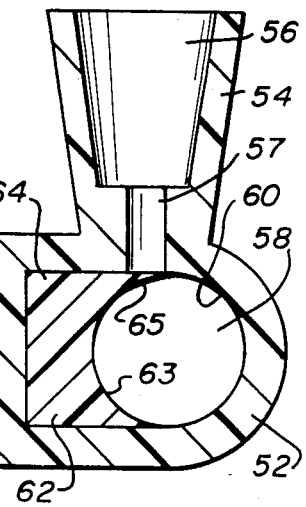
Fig_12
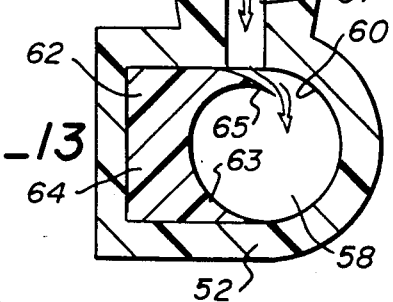
Fig_13
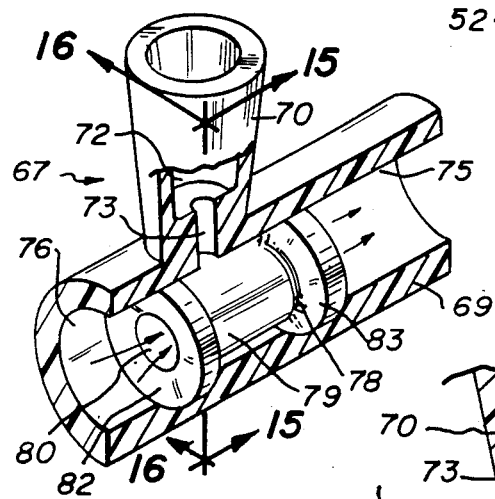
Fig_14
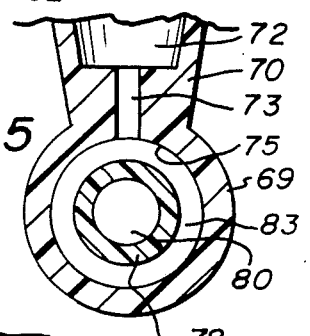
Fig_15
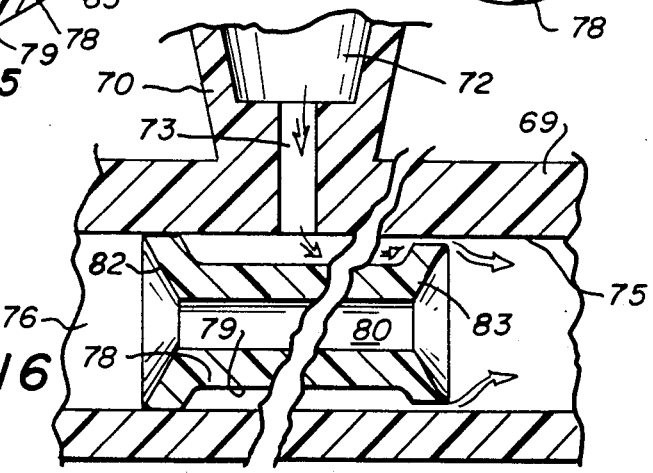
Fig_16

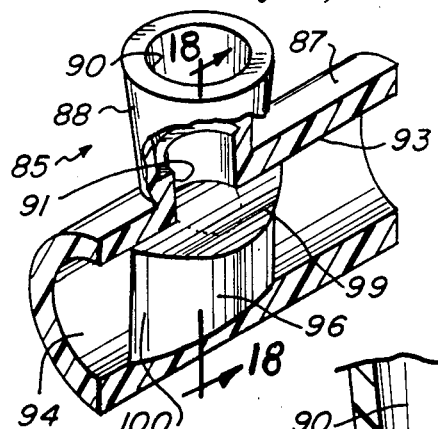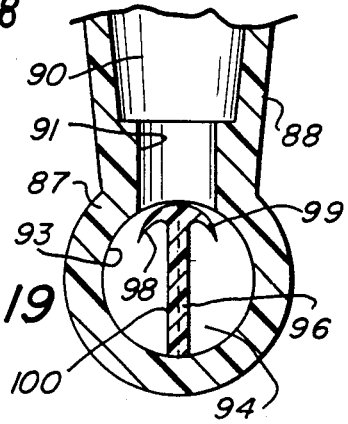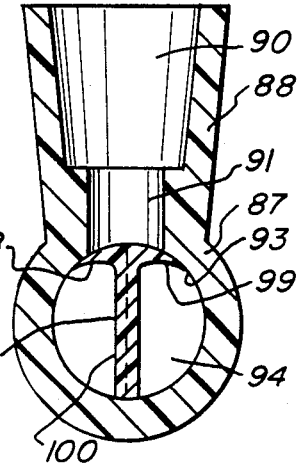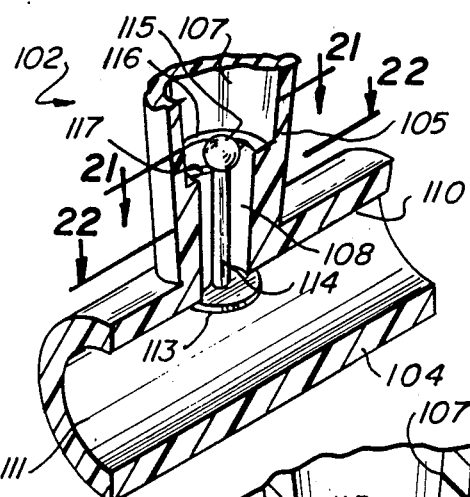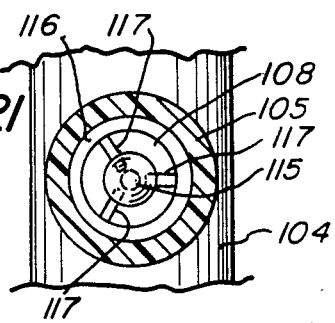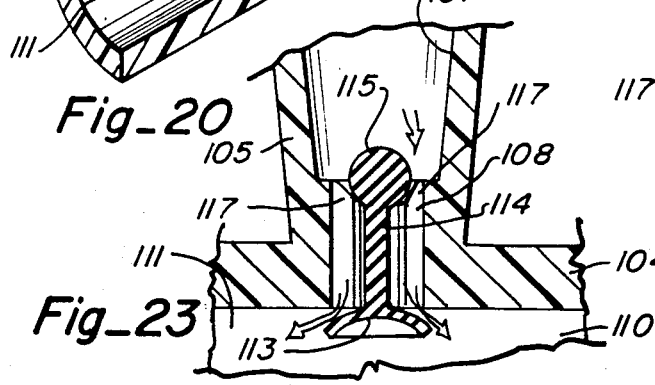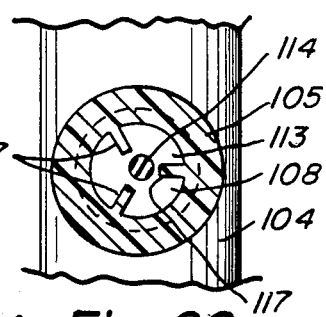

4,666,429

INFUSION DEVICE HAVING IMPROVED VALVING APPARATUS

FIELD OF THE INVENTION

This invention relates to an infusion device, and, more particularly, relates to infusion device having an improved valving apparatus.

BACKGROUND OF THE INVENTION

Infusion devices have heretofore been suggested for use in application of various primary fluids to a patient, and such devices have commonly included a primary conduit for conveying the primary fluid from a primary fluid source to the patient. In addition, at least some such devices have heretofore utilized secondary conduits, connected with the primary conduit through a one-way valve, to add one or more secondary fluids, such as drugs, for example, to the primary fluid being infused into a patient through the primary conduit (see, for example, U.S. Pat. No. 4,447,230).

Such devices, including devices using a one-way valve, have, however, presented a problem in creating an undesirable volumetric dead space at the junction of the secondary conduit to the primary conduit. The disadvantage of creation of such a volumetric dead space is recognized in U.S. Pat. No. 4,439,182, and the device described therein attempts to minimize the created dead space.

It should therefore be appreciated that further improvements in valving apparatus to substantially preclude formation of volumetric dead space at the junction of the primary and secondary conduits is desirable.

SUMMARY OF THE INVENTION

This invention provides an infusion device having an improved valving apparatus formed in a manner such that creation of an undesirable volumetric dead space is substantially precluded. A movable element is utilized in the valving apparatus with the movable element being positioned adjacent to the inner wall of the primary conduit to thus avoid forming of the undesirable dead space at the junction thereof. The movable element is partially displaced to allow introduction of secondary fluid through the valving apparatus to the primary conduit, but is retained in place to prevent flow of primary fluid from the primary conduit into the secondary conduit. Several variations of the movable element are disclosed.

It is therefore an object of this invention to provide an improved infusion device.

It is another object of this invention to provide an infusion device having an improved valving apparatus.

It is still another object of this invention to provide an infusion device having an improved valving apparatus wherein formation of a volumetric dead space is substantially precluded.

It is another object of this invention to provide an infusion device having an improved valving apparatus that provides one-way valving to allow introduction of a secondary substance to a primary conduit while precluding fluid in the primary conduit from entering the secondary conduit.

It is still another object of this invention to provide an infusion device having an improved valving apparatus that includes a movable element positioned adjacent to the inner wall of the primary conduit.

With these and other objects in view, which will become apparent to one skilled in the art as the description proceeds, this invention resides in the novel construction, combination, and arrangement of parts substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate complete embodiments of the invention according to the best mode so far devised for the practical application of the principles thereof, and in which:

FIG. 1 is a side view illustrating an infusion device having primary and secondary fluid conduits with the secondary conduit being connected with the primary conduit through the improved valving apparatus of this invention;

FIG. 2 is a perspective view illustrating a plurality of syringes connected with a primary conduit through the valving apparatus of this invention to thereby allow introduction of a plurality of secondary fluids into the primary conduit;

FIG. 3 is an enlarged and exploded perspective view of the now preferred configuration of the valving apparatus of this invention shown adapted for introducing one or two separate secondary fluids into the primary conduit;

FIG. 4 is an enlarged partial perspective view of the junction of one secondary conduit with the primary conduit as shown in FIG. 3;

FIG. 5 is a side view, partially in schematic, illustrating relative positioning, when assembled, of the valving apparatus, as shown in FIG. 3, for secondary fluid insertion;

FIG. 6 is a sectional view taken through lines 6—6 of FIG. 5;

FIG. 7 is a sectional view taken through lines 7—7 of FIG. 6;

FIG. 8 is a partial sectional view similar to that of FIG. 6 but illustrating partial displacement of the movable element (membrane) to allow fluid from the secondary conduit to enter the primary conduit;

FIG. 9 is a partial sectional view similar to that of FIG. 7 but illustrating partial displacement of the movable element (membrane) to allow fluid from the secondary conduit to enter the primary conduit;

FIG. 10 is an alternate embodiment of the valving apparatus illustrating use of a rib structure to clamp a thin membrane serving as the movable element;

FIG. 11 is a partial perspective view of another alternate embodiment of the valving apparatus illustrating use of a flap as the movable element;

FIG. 12 is a cross-sectional view taken through lines 12—12 of FIG. 11;

FIG. 13 is a cross-sectional view similar to that of FIG. 12 and illustrating partial displacement of the flap to enable flow of secondary fluid into the primary conduit;

FIG. 14 is a partial cut-away perspective view of still another alternate embodiment of the valving apparatus illustrating use of a spool having a displacable shoulder as the movable element;

FIG. 15 is a cross-sectional view taken through lines 15—15 of FIG. 14;

FIG. 16 is a sectional view taken through lines 16—16 of FIG. 14;

FIG. 17 is a partial cut-away perspective view of yet another alternate embodiment of the valving apparatus illustrating use of a T-shaped element as the movable element;

FIG. 18 is a cross-sectional view taken through lines 18—18 of FIG. 17;

FIG. 19 is a cross-sectional view similar to that of FIG. 18 and illustrating partial displacement of the T-shaped element to enable flow of secondary fluid into the primary conduit;

FIG. 20 is a partial cut-away perspective view of still another alternate embodiment of the valving apparatus illustrating use of an anchored disk as the movable element;

FIG. 21 is a sectional view taken through lines 21—21 of FIG. 20;

FIG. 22 is a sectional view taken through lines 22—22 of FIG. 20; and

FIG. 23 is a partial cut-away side view of the valving apparatus shown in FIG. 20 and illustrating displacement of the disk to enable flow of secondary fluid into the primary conduit.

DESCRIPTION OF THE INVENTION

Referring to the drawings, primary conduit 12 is shown in FIG. 1 extending from a source of primary fluid (not shown) to a needle 14 for injection of fluid to a patient therethrough. As shown, primary conduit 12 includes fluid addition device 16, through which secondary fluid can be added to the fluid flowing through the primary conduit. Infusion devices are well known, and have therefore been shown herein only to the extent necessary to better illustrate the invention.

As indicated in FIG. 1, secondary fluid, such as a drug, for example, can be added to the primary fluid by introducing the secondary fluid into the primary conduit at fluid addition device 16. As illustrated, the secondary fluid can be stored in a syringe 18 that is connected with the primary conduit through secondary conduit 19 (which can be the nozzle of the syringe) and valving apparatus 20. Since valving apparatus 20 provides a one-way valve, the primary fluid is precluded from entering the secondary conduit, and hence, even if no syringe is attached to the valving apparatus, as indicated in FIG. 1, no primary fluid will flow therethrough.

Discharge of fluid from syringe 18 is controlled by actuation of piston rod 22. As indicated in FIG. 2, a plurality (four being illustrated) of syringes 18 may be connected with the primary fluid conduit, and flow of fluid from each syringe is individually controlled by separate actuation of each piston rod 22 associated therewith. This can be accomplished, for example, by manual operation of each piston rod 22 or, more preferably, may be accomplished by a drive unit for individually driving each rod, as indicated in FIG. 2, so that an individualized dosage is supplied through the secondary conduits and valving apparatus to the primary conduit. A drive unit to accomplish individual drive of each syringe is described in U.S. patent application Ser. No. 734,028 entitled "Syringe Drive Apparatus and Method", filed May 14, 1985, by David C. Howson et al, and assigned to the assignee of this invention.

Valving apparatus 20, in the now preferred embodiment, is shown in greater detail in FIG. 3. As shown, fluid addition device 16 (which forms a part of the overall valving structure) is illustrated to allow one or two secondary conduits to be connected with the primary conduit established through device 16 (as indicated in FIG. 2, the number of secondary conduits may be increased through the use of additional devices 16, and device 16 could be modified, if desired, to provide additional secondary conduit junctions). Device 16 is preferably formed of polycarbonate material, and is connected with tubing 12 of the primary conduit by means of connectors 24 and 25 having male and female ends 26 and 27, respectively, thereon.

Device, or block 16, has an annular opening 29 at one side thereof for each secondary conduit junction, with each opening 29 being in communication with primary pathway 30 (which pathway establishes the primary conduit through device 16). As best shown in FIG. 4, shoulder 31 extends partially across annular opening 29.

As best shown in FIG. 3, valving apparatus 20 includes a tubular spacer 33, preferably formed of polycarbonate material, having an outer end 34 adapted to connect with secondary conduit 19 (which can be the nozzle of syringe 18, for example). The inner end 35 of spacer 33 is of a size to be snugly received in annular opening 29 of block 16 (as indicated in FIG. 5), and thin membrane 37 is provided between shoulder 31 of block 16 and inner end 35 of spacer 33, as best indicated in FIGS. 3 and 6.

As best shown in FIGS. 6 and 7, thin membrane 37 is clamped between shoulder 31 of device 16 and inwardly directed shoulder 39 of inner end 35 of spacer 33. When secondary fluid is discharged through the secondary conduit, the secondary fluid flows through passage 41 (of spacer 33) and through restrictive passage 42 (adjacent to shoulder 39 of spacer inner end 35) to membrane 37.

Membrane 37 is impervious to liquids, but is pliable and resilient so that, upon application of pressure, the membrane is partially displaced, as indicated in FIGS. 8 and 9, to allow secondary fluid to pass around the edges of the membrane not held clamped by shoulders 31 and 39 to allow the secondary fluid to flow from the secondary conduit into fluid passageway 30. Membrane 37 is preferably formed as a thin disk of thermoplastic material (and may be formed, as is now preferred, from an alloy of polypropylene and craton) having a diameter of about 0.120 inches and a thickness of about 0.021 inches. Membrane 37 provides one-way valving since the membrane is not displaced in the opposite direction due to fluid flow in the primary passageway and hence primary fluid cannot enter the secondary conduit.

As best shown in FIG. 7, membrane 37 is positioned adjacent to inner wall 44 of the primary passageway (as opposed to being adjacent to the outer wall as in the case with at least some prior art devices) so that the membrane is substantially aligned with the inner wall except when secondary fluid is being inserted into the primary conduit. By this positioning of membrane 37, volumetric dead space (or stagnant fluid volume) is eliminated at the junction of the secondary conduit with the primary conduit, and the flow of primary fluid is thus able to purge the entire area at the primary fluid side of the valving (with a stagnant fluid volume, this volume is not so purged).

In operation, primary fluid is supplied as needed to a patient through the primary conduit. When one or more secondary fluids are needed, as, for example, by the needed addition of one or more drugs, one or more syringes are filled with the needed secondary fluid or fluids, and each syringe is positioned with the nozzle extending into a valving apparatus of this invention to thereby connect the syringe with the primary fluid passageway through the valving apparatus. The secondary fluid is then added through the one-way valving apparatus by actuation of the piston rod of each syringe.

A first alternate embodiment 46 of the valving apparatus of this invention is shown in FIG. 10. As shown, shoulder 39 of spacer 33 has a rib 48 thereon that extends inwardly toward shoulder 31 at annular opening 29 of fluid addition device 16. Rib 48 therefore comes into engagement with the edges of membrane 37 clamped between the shoulders 31 and 39 to better hold the edges in place. Membrane 37 is displaced, however, in the same manner as brought out hereinabove to allow one-way valving to occur.

A second alternate embodiment 50 of the valving apparatus is shown in FIGS. 11 through 13. As shown, fluid addition device 52 has secondary inlet 54 therein (one or more secondary inlets can be provided in the same manner as described in connection with conduit 16 of embodiment 20 of the valving apparatus). Inlet 54 includes secondary fluid passage 56 and restricted secondary fluid passage 57, with restricted passage 57 communicating with primary fluid passage 58 so that secondary fluid can flow from a reservoir (not shown), such as in a syringe, through the secondary inlet to the primary passage.

One-way valving for the secondary inlet is provided at inner wall 60 of the primary fluid passage 58. Elastomeric member 62, at primary fluid passage 58, has an inner curved surface 63 and a rectangularly-shaped anchor portion 64 to anchor the elastomeric member 62 within fluid addition device 52 so that curved surface 63 forms a part of the overall inner wall of primary fluid passage 58. The flared edge of elastomeric member 62 provides a flap 65 that extends across restricted passage 57 to form a flexible membrane thereat.

As indicated in FIG. 12, when no secondary fluid is flowing through passages 56 and 57 of secondary inlet 54, flap 65 seals the inlet against flow of fluid from the primary fluid passage 58 into the secondary inlet. As shown in FIG. 13, however, when secondary fluid is caused to flow through secondary inlet passages 56 and 57, flap 65 is displaced inwardly, from its normal position adjacent to the inner wall of the primary fluid passage, to allow the secondary fluid to be inserted into the primary fluid passage.

A third alternate embodiment 67 of the valving apparatus is shown in FIGS. 14 through 16. As shown, fluid addition device 69, which may be similar to fluid addition device 16 as shown in FIG. 3, has secondary inlet 70 therein, which inlet may be identical to that of inlet 54 described in connection with embodiment 50 of the valving apparatus, and which inlet has secondary fluid passage 72 and restricted secondary fluid passage 73 therein.

One-way valving for the secondary inlet is provided at inner wall 75 of primary fluid passage 76. A spool 78 (preferably of elastomeric material) has a central portion 79 that is recessed from inner wall 75 and is hollow to allow primary fluid to pass through central bore 80, first annular shoulder 82 at the upstream end of the spool which engages inner wall 75 at an angle to form a seal thereat, and second annular shoulder 83 at the downstream end of the spool which engages inner wall 75 at an angle to form a seal against passage of fluid from the primary fluid passage to the secondary inlet but allows passage of secondary fluid from the secondary inlet to the primary passage (as indicated in FIG. 16).

A fourth alternate embodiment 85 of the valving apparatus is shown in FIGS. 17 through 19. As shown, fluid addition device 87, which may be similar to fluid addition device 16 as shown in FIG. 3, has a secondary inlet 88 therein, which inlet may be similar to that of inlet 54 described in connection with embodiment 50 of the valving apparatus, and which inlet has secondary fluid passage 90 and restricted secondary fluid passage 91 therein.

One-way valving for the secondary inlet is provided at inner wall 93 of primary fluid passage 94. A T-shaped element 96 (preferably formed of elastomeric material) is provided within passage 94 with arms 98 and 99 of element 96 bridging restricted passage 91 to form a seal thereat, and the end of leg 100 of element 96 enagaging the inner wall of primary passage 94 at the side opposite that of secondary inlet 88 to anchor element 96 and maintain the seal at passage 91 except when arms 98 and 99 are displaced inwardly from inner wall 93 due to secondary fluid flow through the secondary inlet to the primary passage (as indicated in FIG. 19).

A fifth alternate embodiment 102 of the valving apparatus is shown in FIGS. 20 through 23. As shown, fluid addition device 104, which may be similar to fluid addition device 16 as shown in FIG. 3, has a secondary inlet 105 therein, which inlet may be similar to that of inlet 54 described in connection with embodiment 50 of the valving apparatus, and which inlet has secondary fluid passage 107 and restricted secondary fluid passage 108 therein.

One-way valving for the secondary inlet is provided at inner wall 110 of primary fluid passage 111. A disk 113 is positioned at inner wall 110 with disk 113 being of sufficient size to cover restricted secondary fluid passage 108. Arm 114 extends through restricted fluid passage 108. One end of arm 114 is fastened to disk 113 and the other end of arm 114 terminates at ball 115. A retainer 116 has ribs 117 (three as shown) that extend from below ball 115 to disk 113. The ribs thus extend through restricted secondary passage 108, and arm 114 is positioned between the inner edges of the ribs so that the arm is lengthwise movable therebetween. Disk 113, arm 114 and ball 115 are preferably made of elastomeric material and, in conjunction with retainer 116, normally positions and maintains disk 113 against inner wall 110 to establish a seal at the secondary inlet. When secondary fluid is caused to flow through the secondary inlet toward the primary passage, however, disk 113 is partially displaced by the force exerted by the secondary fluid to allow the secondary fluid to enter the primary passage (as indicated in FIG. 23).

In operation, each of the alternate embodiments described herein operate in essentially the same manner as described in connection with embodiment 50 of the valving apparatus. In each case, the movable element is partially displaced due to flow of secondary fluid through the secondary inlet toward the primary fluid passage to allow the secondary fluid to enter the primary passage. At all other times, the movable element blocks the passage of fluid in either direction between the secondary inlet and the primary fluid passage. Also, in each case, the movable element is adjacent to the inner wall of the primary passage to substantially preclude formation of a volumetric dead space.

In view of the foregoing, it is to be appreciated that this invention provides an infusion device having improved valving apparatus.

What is claimed is:

1. An infusion apparatus, comprising:
   a primary conduit for conveying a primary fluid through a primary passage formed by the inner wall of said primary conduit;
   engaging means adjacent to and outside said primary passage;
   a secondary conduit adapted to receive a secondary fluid to be mixed with said primary fluid passing through said primary passage;
   connecting means for connecting said secondary conduit to said primary conduit so that said secondary conduit communicates with said primary passage; and
   valving means having spaced portions engaging said engaging means and a displaceable portion having opposite edges and extending between said spaced portions so that said displaceable portion is displaced upon actuation of said valving means due to fluid flow from said secondary conduit toward said primary conduit, with said spaced portions remaining in contact with said engaging means during said actuation of said valving means, whereby said displaceable portion of said valving means provides openings to said primary conduit from said secondary conduit at both of said opposite edges, said valving means blocking flow of fluid between said primary passage and said secondary conduit except during actuation of said valving means due to flow of secondary fluid through said secondary conduit toward said primary passage to thereby allow said secondary fluid to enter said primary passage, and said displaceable portion of said valving means, when not displaced due to actuation of said valving means, having a surface substantially adjacent to the inner wall of said primary conduit to thereby substantially preclude formation of a volumetric dead space thereat.

2. The apparatus of claim 1 wherein said valving means includes a thin membrane one side of which forms said surface that is substantially adjacent to the inner wall of said primary conduit.

3. The apparatus of claim 1 wherein said connecting means includes an end portion having a shoulder thereat for engaging said spaced portion of said valving means, and wherein said shoulder is recessed from the inner wall of said primary conduit a distance substantially equal to the thickness of said valving means.

4. The apparatus of claim 3 wherein said shoulder has a rib thereon engagable with said membrane.

5. The apparatus of claim 1 wherein said secondary fluid is a drug to be added to primary fluid, wherein said drug is contained within a syringe having a nozzle providing said secondary conduit and a piston to cause discharge of said drug from said syringe through said nozzle, and wherein said connecting means is adapted to receive said nozzle of said syringe whereby said valving means is actuated by movement of said piston discharging said drug from said syringe.

6. The apparatus of claim 1 wherein a plurality of secondary conduits are connected with said primary passage through a plurality of connecting means, with each of said connecting means including a different one of a plurality of said valving means.

7. An infusion apparatus, comprising:
   a primary conduit for conveying a primary fluid through a primary passage formed by the inner wall of said primary conduit;
   a secondary conduit adapted to receive a secondary fluid to be mixed with said primary fluid passing through said primary passage;
   connecting means having a first portion connectable with said secondary conduit and a second portion having a cross-sectional area less than that of said first portion, with said second portion having an end portion opening into said primary passage;
   retaining means extending along an outside said primary passage adjacent to said end portion of said connecting means; and
   valving means having spaced portions positioned between said end portion of said connecting means and said primary conduit and a displaceable portion extending between said spaced portions so that said valving means normally blocks the flow of fluid between said primary passage and said secondary conduit, said displaceable portion of said valving means having opposite edges extending between said spaced portions of said valving means and said displaceable portion being displaced due to flow of secondary fluid through said secondary conduit toward said primary passage, with said spaced portions remaining positioned between said end portion of said connecting means and said primary conduit, to allow said secndary fluid to enter said primary passage, through said valving means at both of said opposite edges of said displaceable portion, and said displaceable portion of said valving means, when not displaced, being substantially adjacent to the inner wall of said primary passage to thereby substantially preclude formation of volumetric dead spaces thereat.

8. The apparatus of claim 7 wherein said valving means is formed from a flexible and resilient material capable of forming a seal between said end portion of said connecting means and said primary passage.

9. An infusion apparatus, comprising:
   a primary conduit for connecting a primary fluid through a primary passage established by the inner wall of said primary conduit to a discharge end portion;
   a secondary conduit adapted to be connected with a syringe to receive a secondary fluid therefrom, which secondary fluid is to be mixed with said primary fluid flowing through said primary passage;
   connecting means for connecting said secondary conduit to said primary passage so that said secondary conduit communicates with said primary passage, said secondary conduit having an end portion that terminates adjacent to the inner wall of said primary passage and with said end portion having shoulder means formed thereat such that said end portion has an inner recessed section; and
   valving means comprising a thin membrane having spaced portions received and retained at said inner recessed section of said end portion of said connecting means so that a displaceable portion of said membrane extends substantially across said end portion adjacent to the inner wall of said primary passage with said displaceable portion of said membrane having opposite edges extending across said primary passage at opposite edges of said membrane, said displaceable portion of said membrane being movable into said primary passage due to the flow of secondary fluid through said secondary conduit toward said primary passage to allow said secondary fluid to enter said primary passage at both of said opposite edges of said displaceable portion of said membrane, and said membrane being immovable to flow through said primary passage toward said secondary conduit to thereby preclude passage of primary fluid to said secondary conduit, with said membrane, except while having said displaceable portion displaced due to said flow of secondary fluid toward said primary passage, being substantially aligned with the inner wall of said primary passage to thereby preclude formation of a volumetric dead space thereat.

10. The apparatus of claim 9 wherein said spaced portions of said membrane are clamped at said inner recessed section.

11. The apparatus of claim 9 wherein said primary passage includes an intermediate section adapted to receive at least one secondary conduit, with said intermediate section having an annular opening therein to receive said end portion of said connecting means wherein said membrane is positioned between said end portion and said annular opening, said annular opening being larger than the diameter of said primary passage so that a shoulder extends from the inner wall of said primary passage to said annular opening, and wherein said membrane is clamped between said shoulder and said end portion of said connecting means.

* * * * *